(12) United States Patent
Wöldike et al.

(10) Patent No.: US 6,329,176 B1
(45) Date of Patent: Dec. 11, 2001

(54) METHOD FOR THE PRODUCTION OF FACTOR VII

(75) Inventors: Helle Wöldike, Lynge; Finn Wiberg, Farum; Lars Søegaard Nielsen, Nivå, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/558,027

(22) Filed: Apr. 25, 2000

Related U.S. Application Data

(63) Continuation of application No. PCT/DK99/00607, filed on Nov. 5, 1999.
(60) Provisional application No. 60/108,065, filed on Nov. 12, 1998.

(30) Foreign Application Priority Data

Nov. 6, 1998 (DK) .................................................. 01436/98
Nov. 9, 1998 (DK) .................................................. 01439/98

(51) Int. Cl.$^7$ ...................................................... C12P 21/02
(52) U.S. Cl. ............................................................ 435/69.6
(58) Field of Search ................................. 435/69.1, 69.6, 435/70.3; 530/412

(56) References Cited

U.S. PATENT DOCUMENTS

| | | | |
|---|---|---|---|
| 5,460,950 | 10/1995 | Barr et al. | 435/69.1 |
| 5,516,650 | 5/1996 | Foster et al. | 435/68.1 |

FOREIGN PATENT DOCUMENTS

| | | | |
|---|---|---|---|
| 0 319 944 | 6/1989 | (EP) | . |
| 0 548 012 B1 | * 3/1997 | (EP) | . |

OTHER PUBLICATIONS

Hagen et al. Proc. Natl. Acad. Sci. USA, 83:2412–2416, 1986.*

Mather. in Goeddel et al., Gene Expression Technology, Methods in Enzymology vol. 185, 1990, p. 576.*

* cited by examiner

*Primary Examiner*—James Ketter
*Assistant Examiner*—Lisa Gansheroff
(74) *Attorney, Agent, or Firm*—Reza Green, Esq.

(57) ABSTRACT

Disclosed is a method for high efficiency release of recombinant proteins in eukaryotic cells and more specifically, for enhancing the secretion of Factor VII by co-expression of kex2 endoprotease with FVII in cells of mammalian origin.

8 Claims, 1 Drawing Sheet

METHOD FOR THE PRODUCTION OF FACTOR VII

CROSS-REFERENCES TO RELATED APPLICATIONS

The present application is a continuation of PCT/DK99/00607 filed Nov. 5, 1999 and claims priority under 35 U.S.C. 119 of U.S. provisional application no. 60/108,065 filed Nov. 12, 1998 and Danish application nos. PA 1998 01439 filed Nov. 9, 1998 and PA 1998 01436 filed Nov. 6, 1998, the contents of which are fully incorporated herein by reference.

BACKGROUND OF THE INVENTION

1. Field of the Invention

The present invention relates to a method for high efficiency release of recombinant proteins in eukaryotic cells or more specifically, for enhancing the secretion of Factor VII by co-expression with Kex2 endoprotease in cultured cells of mammalian origin.

2. Description of the Related Art

Advances in cell culture and recombinant DNA technologies have facilitated the expression of a variety of proteins of therapeutic or other economic value using genetically engineered cells. The expression of many biologically active therapeutic proteins, which are derived from higher eukaryotic sources, often requires specific post-translational modifications which do not naturally occur in lower eukaryotic or prokaryotic cells, thus necessitating the use of cells derived from higher eukaryotic sources. For example, the expression of glycoproteins in mammalian cells has the advantage of providing proteins that contain natural glycosylation. Mammalian-produced glycoproteins contain outer chain carbohydrate moieties which are markedly different from the outer chain carbohydrate moieties present on glycoproteins produced from lower eukaryotes. The use of mammalian cells as hosts for the production of secreted mammalian proteins has the significant advantage over secretion from lower eukaryotes in that mammalian cells have a secretory system that readily recognizes and properly processes secretion-directed proteins, which is not necessarily true for lower eukaryotes.

Efficient expression of coding sequences in eukaryotic hosts may also require the expression of associated proteins that are required for the processing, stabilization or modification of the protein to achieve biological activity. Optimal expression of biologically active recombinant proteins may also be dependent upon the presence of specific translation and/or transcription factors. These proteins may be present in host cells at such low levels that efficient expression of recombinant proteins is limited. Examples of proteins that require specific post-translational modification include certain coagulation factors, which require gamma-carboxylation of specific glutamic acid residues for biological activity and may also require the conversion of specific aspartic acid residues to beta-hydroxy aspartic acid for biological activity.

Blood coagulation is a process consisting of a complex interaction of various blood components, or factors, which eventually give rise to a fibrin clot. Generally, the blood components which participate in the so-called coagulation cascade are proenzymes or zymogens, enzymatically inactive proteins which are converted to proteolytically active enzymes by the action of an activator which in itself is an activated clotting factor. Coagulation factors that have undergone such a conversion and generally referred to as active factors are designated by adding a lower case "a" suffix (e.g. Factor VIIa).

Factor VII is a trace plasma glycoprotein that circulates in blood as a single-chain zymogen. The zymogen is catalytically inactive (Williams et al., *J. Biol. Chem.* 264, 1989, pp. 7536–7543; Rao et al., *Proc. Natl. Acad. Sci. USA* 85, 1988, pp. 6687–6691). Single-chain Factor VII may be converted to two-chain Factor VIIa by Factor Xa, Factor XIIa, Factor IXa or thrombin in vitro. Factor Xa is believed to be a major physiological activator of Factor VII. Like several other plasma proteins involved in hemostasis, Factor VII depends on vitamin K for expression in an active form, vitamin K being required for the γ-carboxylation of multiple glutamic acid residues clustered in the N-terminus of the protein. The γ-carboxyglutamic acid (Gla)-containing domain is followed by two domains that are homologous to the epidermal growth factor precursor (EGF) whereas the serine protease part occupies the C-terminal half of the molecule.

Proteins involved in the coagulation cascade are also often processed to mature proteins by cleavage at dibasic amino acid residues. Thus, Factor VII is synthesized with an N-terminal 38 amino acids propeptide, which is cleaved off C-terminally to two pairs of arginins (R-R-R-R). There are several candidate enzymes which might be involved in this processing in vivo, some of which operate preferentially in the endoplasmic reticulum (ER) and some in the Golgi apparatus in a membrane bound form.

Another important post-translational modification of Factor VII is gamma-carboxylation of 10 glutamic acid residues located close to the cleavage point of the propeptide. The sequence of events is indicated by the fact that the presence of the propeptide and the correct sequence of it seems important for the process of gamma-carboxylation (Busby et al., Curr. Adv. in Vit. K. Res. 173–181 (1987) and Ul-rich et al., J. Biol. Chem. 263 (20) 9697–9702 (1988)), which occurs in the ER catalyzed by a membrane-bound carboxylase.

Kex2 endoprotease of Saccharomyces yeast is a protease that specifically processes the precursor of mating type α-factor and a killer factor. The properties of the Kex2 endoprotease are reported to be the following: (1) Kex2 cleaves at the C-terminal of Lys-Arg sequence for excision of mating type α-factor from its precursor, and at the C-terminal of Lys-Arg sequence and Pro-Arg sequence to release mature killer factor; (2) a purification thereof was attempted, and it was found that the enzyme is present in a membrane fraction and requires calcium ions for activation thereof; (3) Kex2 is a glycoprotein having a molecular weight of 100 to 120 K Dalton; (4) Kex2 specifically cleaves at the C-terminal of sequences Arg-Arg, Lys-Arg, and Pro-Arg (BBRC, 144, 807–814, 1987).

In WO 90/01550 plasmids are disclosed carrying polycistronic expression units including an intercistronic leader. In U.S. Pat. No. 5,460,950 host cells are disclosed expressing PACE, a human endoprotease, capable of cleaving precursor polypeptides where the PACE encoding sequence and the precursor polypeptide encoding sequence is operably linked to an expression control sequence permitting co-expression of the two sequences.

SUMMARY OF THE INVENTION

The present invention is related to a method for producing Factor VII comprising
a) cultivating a mammalian cell line comprising a DNA sequence encoding a yeast endoprotease or a derivative thereof and a DNA sequence encoding FVII in a suitable culture medium; and
b) isolating Factor VII from the medium.

According to one embodiment of the present invention, the yeast endoprotease is preferably derived from a Saccharomyces strain and is preferably a Kex2 like endoprotease. The yeast endoprotease may be truncated at its C-terminal end thereby being deprived of its transmembrane region. Further, an ER retention signal may be added to the C-terminal end of the truncated endoprotease. The yeast endoprotease is preferably the Kex2 endoprotease from *Saccharomyces cerevisiae*.

The culture medium is preferably a serum free medium and the mammalian cell line is preferably a CHO cell line or a BHK cell line.

DETAILED DESCRIPTION OF THE INVENTION

Definitions

Figure 1:
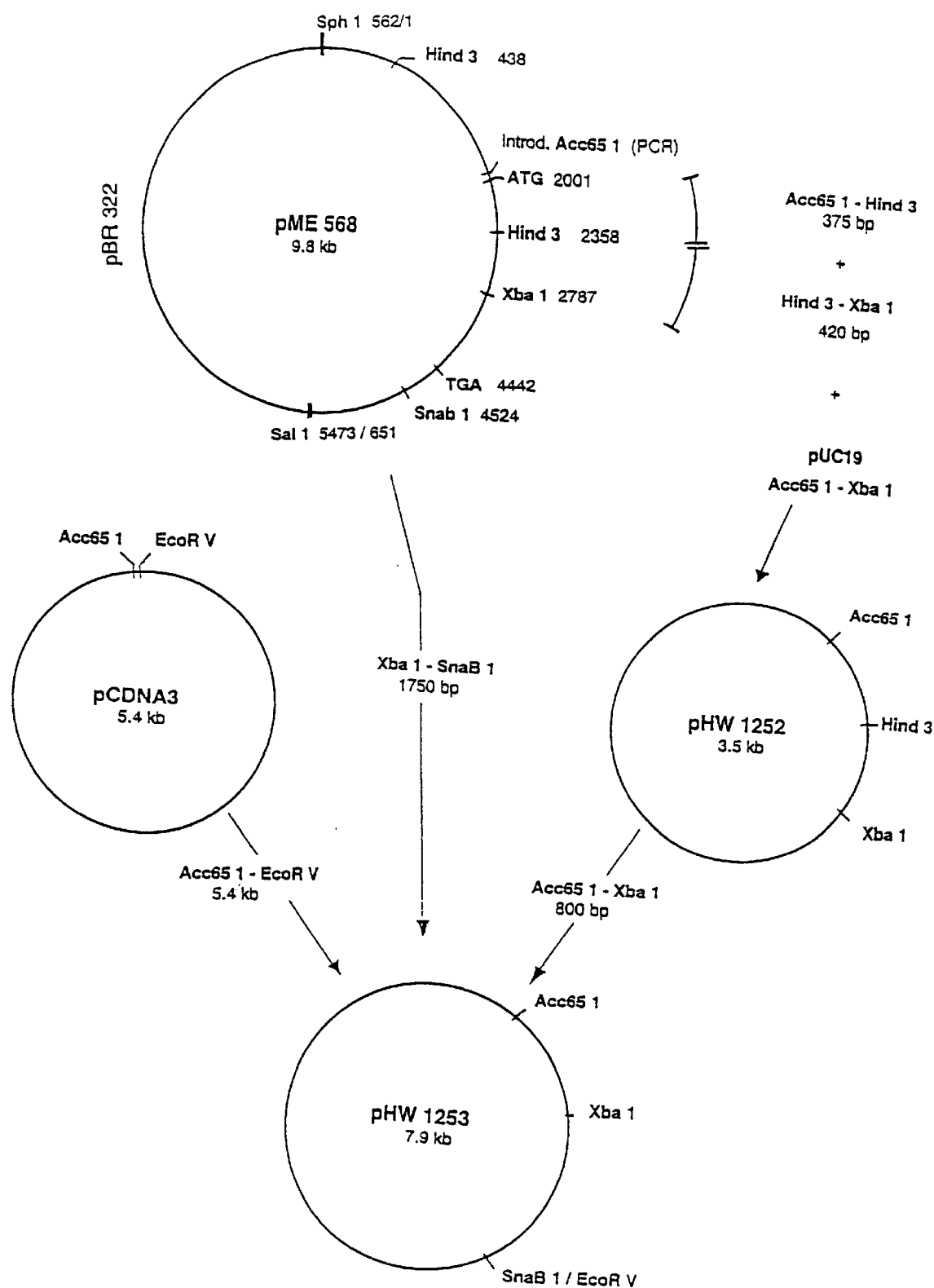
FIG. 1 outlines the construction of the Kex2 expression plasmid using pcDNA3 from Invitrogen as expression cassette.

As used herein the term "KEX2" means the yeast endoprotease gene from *S. cerevisiae*.

As used herein the term "Kex2" means the yeast endoprotease gene product from *S. cerevisiae*.

As used herein the term "full length Kex2" means the complete sequence of Kex2 from amino acid 1 to 814.

As used herein the term "truncated Kex2" means a Kex2 enzyme where the C-terminal end has been removed, in particular from amino acid 814 to amino acid 614 or 675, respectively.

As used herein the term "ER" means Endoplasmatic Reticullum.

As used herein the term "ER retention signal" means KDEL at the C-terminal.

As used herein the term "a Kex2 like endoprotease" means a yeast endoprotease with an amino acid sequence which has a degree of homology to the amino acid sequence of full length Kex2 of at least about 50%, preferably at least about 80%, more preferably at least about 90%, even more preferably at least about 95%. The amino acid sequences of the Kex2 like yeast endoprotease may differ from the amino acid sequence of full length Kex2 by insertion or deletion of one or more amino acid residues and/or substitution of one or more amino acid residues in the natural sequence by different amino acid residues. Preferably, amino acid changes are of a minor nature, that is, conservative amino acid substitutions that do not significantly affect the folding and/or the activity of the endoprotease. Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine) and small amino acids (such as glycine, alanine, serine, threonine and methionine). Amino acid substitutions that do not generally alter the specific activity are known in the art and are described, e.g., by H. Neurath and R. L. Hill, 1979, In, The Proteins, Academic Press, New York. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

With the term "a derivative of an yeast endoprotease" is meant a C-terminally truncated sequence which may contain an ER retention signal attached to the C-terminal end.

The method according to the present invention generally comprises:

(a) introducing into the mammalian cell line a vector system(s) comprising DNA encoding an endoprotease and DNA encoding Factor VII; and (b) growing the transfected mammalian cells in an appropriate medium; and (c) isolating Factor VII from the medium.

The vector system will preferably comprise two separate vectors being capable of expressing FVII and the endoprotease, respectively. In this embodiment of the present invention, the mammalian cells are co-transfected with the two vectors and then cultured in a suitable culture medium. Alternatively an already established Factor VII expression clone may be transfected with a vector capable of expressing the endoprotease. The vector system may also comprise one single vector comprising the FVII expression cassette and the endoprotease expression cassette.

The mammalian cells used as host cells in the method of the present invention include Chinese hamster ovary (CHO) cells, HeLa cells, baby hamster kidney (BHK) cells, COS cells, HEK 293 cells or any number of other immortalized cell lines available, e.g., from the American Type Culture Collection.

Examples of suitable mammalian cell lines are the COS (ATCC CRL 1650), BHK (ATCC CRL 1632, ATCC CCL 10), CHL (ATCC CCL39), HEK 293 (ATCC CRL 1573) or CHO (ATCC CCL 61) cell lines. Methods of transfecting mammalian cells and expressing DNA sequences introduced in the cells are described in e.g. Kaufman and Sharp, *J. Mol. Biol.* 159 (1982), 601–621; Southern and Berg, *J. Mol. Appl. Genet.* 1 (1982), 327–341; Loyter et al., *Proc. Natl. Acad. Sci. USA* 79 (1982), 422–426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841–845.

The vector may be any vector that may conveniently be subjected to recombinant DNA procedures, and the choice of vector will often depend on the host cell into which it is to be introduced. Thus, the vector may be an autonomously replicating vector, i.e., a vector that exists as an extra chromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. The vector is preferably an expression vector in which the encoding DNA sequence is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g., transcription initiates in a promoter and proceeds through the DNA sequence coding for the polypeptide.

The promoter may be any DNA sequence that shows transcriptional activity in the host cell and may be derived from genes encoding proteins either homologous or heterologous to the host cell. Examples of suitable promoters for directing the transcription of the encoding DNA in mammalian cells are the SV40 promoter (Subramani et al., *Mol. Cell Biol.* 1 (1981), 854–864), the MT-1 (metallothionein gene) promoter (Palmiter et al., *Science* 222 (1983), 809–814) or the adenovirus 2 major late promoter.

centrifugation or filtration, precipitating the proteinaceous components of the supernatant or filtrate by means of a salt, e.g., ammonium sulfate, purification by a variety of chromatographic procedures, e.g., ion exchange chromatography, gel filtration chromatography, affinity chromatography, or the like, dependent on the type of polypeptide in question.

The following examples are offered by way of illustration, not by way of limitation.

EXAMPLE 1
Construction of KEX2 Expression Plasmid

FIG. 1 outlines the construction of the Kex2 expression plasmid using pcDNA3 from Invitrogen as expression cassette.

From a genomic clone of KEX2 in plasmid pME568, the N-terminal 800 bp's of the coding region was subcloned into pUC 19 Acc651-Xba1 after introduction of an Acc651 site 15 bp's upstream of the initial ATG by PCR of the N-terminal 375 bp's using the primers:

```
Downstream    5' ACCTGGTACCCCATTATAAGATGAAAG 3'    (SEQ ID NO:1)
                   Acc651

Upstream      5' GGTAACAAGCTTGAGTCC 3'             (SEQ ID NO:2)
                       Hind3
```

The encoding DNA sequence may also be operably connected to a suitable terminator, such as the human growth hormone terminator (Palmiter et al., op cit.) or the ADH3 (McKnight et al., op. ) terminator.

The vector may further comprise elements such as polyadenylation signals (e.g., from SV40 or the adenovirus 5 Elb region), transcriptional enhancer sequences (e.g., the SV40 enhancer) and translational enhancer sequences (e.g,. the ones encoding adenovirus VA RNAs).

The vector will also preferably contain a signal peptide coding region, which codes for an amino acid sequence linked to the amino terminus of the FVII polypeptide which can direct the expressed FVII polypeptide into the cell's secretory pathway of the host cell. The signal may be homologous or heterologous to the host mammalian cell line and it may be the natural signal peptide Finally, the vector may comprise a DNA sequence enabling it to replicate in the host cell in question. An example of such a sequence in a mammalian cell is the SV40 origin of replication.

The transfected mammalian cells are cultured in a suitable nutrient medium under conditions permitting the co-expression of FVII and the endoprotease whereupon FVII is recovered from the culture medium. The medium used to culture the mammalian cells may be any conventional medium suitable for growing mammalian cells, such as minimal or complex media containing appropriate supplements. Suitable media are available from commercial suppliers or may be prepared according to published recipes (e.g,. in catalogues of the American Type Culture Collection). FVII produced by the cells may then be recovered from the culture medium by conventional procedures including separating the host cells from the medium by This 375 bp's Acc651 -Hind3 fragment was ligated to the adjacent 420 bp's Hind3-Xba1 fragment and cloned into pUC19. From the resulting plasmid, pHW1252, the 800 bp Acc651-Xba1 fragment was excised and inserted with the C-terminal 1750 bp Xba1-SnaB1 fragment from pME568 into pcDNA3 Acc651-EcoRV 5.4 kb to yield the expression plasmid pHW1253. The sequence of KEX2 in pHW1253 is essentially as described in Philippsen,P. et al. Nature 387 (suppl.), 93–98 (1997) in The Yeast Genome Directory.

EXAMPLE 2
Co-expression of Kex2 with FVII

Baby Hamster Kidney (BHK) cells expressing FVII (Berkner et al., Cold Spring Harbor Symp. Quant. Biol. 51, 531–541 (1986)) were transfected with 2 μg plasmid pHW1 253 as described in Example 1, using LipoFect Amine method as described by the supplier (Gibco,Life Technologies, Roskilde, Denmark). Stable clones were selected in medium (Du Ibecco's modified Eagle's medium, 10% fetal calf serum,100 IU penicillin, 100 IU streptomycin 1 mmol/l Na-pyrovate and 5 mg/l vitamin K1) containing 1 mg/l Geneticin G418 (Gibco). After selection, stable clones were picked using cloning cylinders and maintained at 37° C. in an atmosphere containing 5% $CO_2$.

Stable clones were screened in a FVII-ELISA (Novo Nordisk) for FVII production. The Kex2 enzyme activity from 1 million cells of the above clones was determined essentially as described by N. C. Rockwell, G. T. Wang ,G. A. Kraft, and R. S. Fuller., Biochemistry 36 (7) :1912–1917, 1997. The original FVII producing cell line was cultivated in parallel and used as a reference.

We are seeing a positive correlation between Kex 2 expression and secretion of FVII in this BHK cell line, with 2–3 times more FVII produced in the clones co-expressing Kex2.

EXAMPLE 3
Construction of FVII Expression Plasmid

A FVII cDNA with deleted non-translated regions was prepared by PCR with Taq polymerase using the following primers:

```
AAC GGA TCC ACC ATG GTC TCC CAG GCC CTC AGG         (SEQ ID NO:3)
ACG GAA TTC ACT AGT CTA GGG AAA TGG GGC TCG CAG GA  (SEQ ID NO:4)
``` and the human FVII cDNA as a template (Hagen et al. *Proc. Natl. Acad. Sci. USA* 83, 1986, pp. 2412–2416). The PCR fragment was cloned into the vector pBluescript II KS+ (Stratagene) and the sequence was verified. The cDNA was transferred as a BamHI-SpeI fragment to the mammalian cell expression vector Zem219b (Busby et al. *J. Biol. Chem.* 266, 1991, pp.15286–15292), which carries a mouse metallothionin in promoter for driving the inserted cDNA and the dihydrofolate reductase cDNA driven by an SV40 promoter for use as a selectable marker. The resulting plasmid was designated pLN174.

EXAMPLE 4
FVII-transfection of CHO Cells With And Without The KEX2 cDNA and Measurement of FVII Production From Transfected Cells CHO-K1 cells (ATCC CCL 61) adapted for growth in suspension were transfected with:

a. The FVII expression plasmid pLN174 (example a) and the expression vector pcDNA3 (InVitrogen) without inserted cDNA.

b. The FVII expression plasmid pLN174 (example a) and the pcDNA3/KEX2 expression vector using the Qiafect transfection reagent. Double transfectants were selected using 1 $\mu$M methotrexate and 700 $\mu$g/ml Geneticin (GIBCO). When clones were visible by the naked eye the cultures were transferred to T-flasks for further culture.

Pools of transfectants (a and b as described above) were seeded in T25 flasks (0.25×$10^6$ cells per flask) for measurement of FVII production. When the cells adhered to the substrate, fresh medium was added containing 5 $\mu$g/ml of vitamin K1. Culture medium was harvested after 2 further days and assayed for FVII activity with an ELISA kit (DAKO). As can be seen from the table below cotransfection of pcDNA3/KEX2 and FVII gives a 5 times increased expression level of FVII immuno-reactivity as compared to when FVII is cotransfected with the pcDNA3 vector alone.

| Cell type | Plasmids used for transfection | FVII concentration $\mu$g/ml |
|---|---|---|
| a | pLN174/pcDNA3 | 0.18 |
| b | pLN174/pcDNA3 + KEX2 | 0.90 |

What is claimed is:

1. A method for producing Factor VII comprising (a) cultivation of a mammalian cell line comprising a DNA sequence encoding yeast KEX2 endopratease and a DNA sequence encoding Factor VII (FVII) in a suitable culture medium, under conditions in which both said KEX2 endoprotease and said FVII are expressed; and (b) isolation of Factor VII from the medium.

2. The method of claim 1, wherein the culture medium is a serum free medium.

3. The method of claim 1 wherein the mammalian cell line is a CHO cell line.

4. The method of claim 1 wherein the mammalian cell line is a BHK cell line.

5. The method of claim 1 wherein the mammalian cell line is a HEK 293 cell line.

6. A method for producing Factor VII comprising (a) cultivation of a mammalian cell line comprising a DNA sequence encoding (i) a variant of yeast KEX2 endoprotease, wherein said variant is selected from the group consisting of KEX2 1-614 and KEX2 1-675, and (ii) a DNA sequence encoding Factor VII (FVII) in a suitable culture medium, under conditions in which both said KEX2 endopratease and said FVII are expressed; and (b) isolation of Factor VII from the medium.

7. The method of claim 6, wherein the mammalian cell is selected from the group consisting of CHO, BHK, and HEK293 cells.

8. The method of claim 6, wherein the culture medium is a serum-free medium.

* * * * *

SEQUENCE LISTING

<160> NUMBER OF SEQ ID NOS: 4

<210> SEQ ID NO 1
<211> LENGTH: 27
<212> TYPE: DNA
<213> ORGANISM: Saccharomyces cerevisiae

<400> SEQUENCE: 1
acctggtacc ccattataag atgaaag        27

<210> SEQ ID NO 2
<211> LENGTH: 18
<212> TYPE: DNA
<213> ORGANISM: Saccharomyces cerevisiae

<400> SEQUENCE: 2
ggtaacaagc ttgagtcc        18

<210> SEQ ID NO 3
<211> LENGTH: 33
<212> TYPE: DNA
<213> ORGANISM: Saccharomyces cerevisiae

<400> SEQUENCE: 3
aacggatcca ccatggtctc ccaggccctc agg        33

```
<210> SEQ ID NO 4
<211> LENGTH: 38
<212> TYPE: DNA
<213> ORGANISM: Saccharomyces cerevisiae

<400> SEQUENCE: 4
acggaattca ctagtctagg gaaatggggc tcgcagga                              38
```